(12) United States Patent
Moulton

(10) Patent No.: US 7,053,232 B2
(45) Date of Patent: May 30, 2006

(54) LEWIS ACID IONIC LIQUIDS

(75) Inventor: Roger Moulton, Austin, TX (US)

(73) Assignee: Sachem, Inc., Austin, TX (US)

( * ) Notice: Subject to any disclaimer, the term of this patent is extended or adjusted under 35 U.S.C. 154(b) by 310 days.

(21) Appl. No.: 10/642,437

(22) Filed: Aug. 15, 2003

(65) Prior Publication Data

US 2004/0122229 A1 Jun. 24, 2004

Related U.S. Application Data

(60) Provisional application No. 60/404,202, filed on Aug. 16, 2002.

(51) Int. Cl.
C07F 5/06 (2006.01)

(52) U.S. Cl. .................. 556/174; 556/178; 556/180; 556/186

(58) Field of Classification Search ............... 556/174, 556/178, 180, 186
See application file for complete search history.

(56) References Cited

U.S. PATENT DOCUMENTS

| | | | |
|---|---|---|---|
| 2,072,085 A | 3/1937 | Groote et al. | |
| 2,181,087 A | 11/1939 | Caryl et al. | |
| 2,446,331 A | 8/1948 | Hurley | |
| 2,507,030 A | 5/1950 | Lynch et al. | |
| 3,418,216 A * | 12/1968 | Dotzer | 205/234 |
| 4,463,071 A | 7/1984 | Gifford et al. | |
| 4,572,769 A | 2/1986 | Shimizu | |
| 4,628,023 A | 12/1986 | Cawston et al. | |
| 4,714,530 A | 12/1987 | Hale et al. | |
| 4,764,440 A | 8/1988 | Jones et al. | |
| 4,776,929 A | 10/1988 | Aoyama | |
| 4,820,621 A | 4/1989 | Tanka et al. | |
| 4,857,238 A * | 8/1989 | Tsuchiya et al. | 562/820 |
| 4,882,244 A | 11/1989 | Donahue et al. | |
| 4,913,828 A | 4/1990 | Caswell et al. | |
| 4,915,854 A | 4/1990 | Mao et al. | |
| 4,919,839 A | 4/1990 | Durbut et al. | |
| 5,135,825 A | 8/1992 | Mori et al. | |
| 5,273,840 A | 12/1993 | Dominey | |
| 5,286,354 A | 2/1994 | Bard et al. | |
| 5,415,857 A | 5/1995 | Robbins et al. | |
| 5,543,522 A | 8/1996 | Kawahara et al. | |
| 5,565,060 A | 10/1996 | Austin et al. | |
| 5,683,832 A | 11/1997 | Bonhote et al. | |
| 5,827,602 A | 10/1998 | Koch et al. | |
| 5,853,555 A | 12/1998 | Shafifian et al. | |
| 5,870,275 A | 2/1999 | Shiono et al. | |
| 5,910,237 A | 6/1999 | Moulton et al. | |
| 5,929,009 A | 7/1999 | Gambogi | |
| 5,951,845 A | 9/1999 | Moulton | |
| 5,965,054 A | 10/1999 | McEwen et al. | |
| 5,968,338 A | 10/1999 | Hulme et al. | |
| 5,981,474 A | 11/1999 | Manning et al. | |
| 6,165,259 A | 12/2000 | Hallstrom et al. | |
| 6,306,805 B1 | 10/2001 | Bratescu et al. | |
| 6,379,634 B1 | 4/2002 | Fields | |
| 6,406,677 B1 | 6/2002 | Carter et al. | |
| 6,468,495 B1 | 10/2002 | Fields | |
| 2002/0010291 A1 | 1/2002 | Murphy | |
| 2002/0015883 A1 | 2/2002 | Hilarius | |
| 2002/0015884 A1 | 2/2002 | Schmidt | |
| 2002/0055045 A1 | 5/2002 | Michot | |

FOREIGN PATENT DOCUMENTS

| | | |
|---|---|---|
| GB | 1031839 * | 6/1966 |
| WO | WO 95/21871 | 8/1995 |
| WO | WO 95/21872 | 8/1995 |
| WO | WO 98/06106 | 2/1998 |
| WO | WO 99/14160 | 3/1999 |
| WO | WO 01/03211 | 1/2001 |
| WO | WO 01/13379 | 2/2001 |
| WO | WO 01/15175 | 3/2001 |
| WO | WO 01/40146 | 6/2001 |
| WO | WO 02/26701 A2 | 4/2002 |

OTHER PUBLICATIONS

Westmoreland, Jr. et al., Journal of Organometallic Chemistry, vol. 25, No. 2, pp. 329–335 (1970).*

Symmes, Jr. et al., Journal of Organic Chemistry, vol. 43, No. 6, pp. 1250–1253 (1978).*

Westmoreland, Jr. et al., Journal Organometallic Chemistry, Dec. 1970, vol. 25, No. 2, pp. 329–335, especially compound 2 at p. 1251.

Symmes, Jr. et al., Journal of Organic Chemistry, 1978, vol. 43, No. 6, pp. 1250–1253, especially compound 2 at p. 1251.

Xu, Wu and Angell, Austen, "Novel Orthoborate Ionic Liquids," Dept. of Chem., Arizona State University, (date unknown, earlier than Nov. 7, 2002).

Freemantle, Michael, "Designer Solvents Ionic Liquids May Boost Clean Technology Development," Science/Technology, Mar. 30, 1998.

Freemantle, Michael, "Eyes on Ionic Liquids,".Science/Technology, May 15, 2000.

Holbrey, J.D., "Ionic Liquids," Clean Products and Processes, p. 223–236, (1999).

(Continued)

*Primary Examiner*—Porfirio Nazario-Gonzalez
(74) *Attorney, Agent, or Firm*—Renner, Otto, Boisselle & Sklar, LLP

(57) ABSTRACT

The present inventions relate to novel ionic liquids comprising a Lewis acid anion such as $Al_yR_{3y+1}$ wherein y is greater than 0 and R is independently selected from the group consisting of an alkyl group and halogen group. The cation of the ionic liquids can be selected from ammonium, sulfonium, and phosphonium cations wherein said cation generally has less than 14 total carbon atoms. The anion may contain an organic bridge to bond neighboring aluminum atoms that would otherwise be susceptible to leaching aluminum trichloride. The ionic liquids are useful in many applications and particularly as catalysts.

27 Claims, No Drawings

OTHER PUBLICATIONS

Seddon, Kenneth, R., "Room–Temperature Ionic Liquids: Neoteric Solvents For Clean Catalysis," School of Chemistry, The Queens' University of Belfast (date unknown).

Barthel, J., et al., "Lithium Bis [5–fluoro–2–olate–1–benzenesulfonato (2–)–O,O'] borate (1–), a New Anodically and Cathodically Stable Salt for Electrolytes of Lithium–Ion Cells," J. Electrochem. Soc, vol. 145, No. 2, Feb. 1998.

Barthel, J., et al., "A New Class of Electrochemically and Thermally Stable Lithium Salts for Lithium Battery Electrolytes," J. of the Electrochemical Soc., 147 (1) 21:24 (2000).

Barthel, J., et al., "A New Class of Electrochemically and Thermally Stable Lithium Salts for Lithium Battery Electrolytes," J. Electrochem. Soc., vol. 144, No. 11, Nov. 1997.

Barthel, J., et al., "A New Class of Electrochemically and Thermally Stable Lithium Salts for Lithium Battery Electrolytes," J. Electrochem, Soc., vol. 143, No. 11, Nov. 1996.

Barthel, J., et al., "A New Class of Electrochemically and Thermally Stable Lithium Salts for Lithium Battery Electrolytes," J. Electrochem. Soc., vol. 142, No. 8, Aug. 1995.

Scientific American Proteomics Biotech's Next Big Challenge, Apr. 2002.

Khadilkar, et al., "Microwave assisted synthesis of room temperature Ionic liquid precursor quaternary salts in closed vessel," Fifth International Electronic Conference on Synthetic Organic Chemisty (ECSOC–5), 2001.

Wasserscheid, P., et al., "Ionic Liquids in Synthesis," selected pages, Nov. 2002.

Wadhawan, Jay, D., et al, "Ionic liquid modified electrodes," Journal of Electroanalytical Chemistry, 2000.

Elruth, M. K.E. Johnson, Y. Patell, and R.D. Simank, "Reactions of alkanes and cycloakanes in ambient–temperature ionic liquids", International George Papatheodorou Symposium (unkown date of publication; printout from internet date indicated as Mar. 20, 2002).

* cited by examiner

LEWIS ACID IONIC LIQUIDS

RELATED APPLICATION DATA

The present application claims priority to U.S. Provisional Application No. 60/404,202, filed Aug. 16, 2002.

FIELD OF THE INVENTIONS

The present inventions pertain to compositions comprising a Lewis acid ionic liquid and processes for making same.

BACKGROUND AND SUMMARY OF THE INVENTIONS

Ionic liquids are salts that are liquid at ambient or near ambient temperatures (i.e., having a melting point, or melting range, below about 100° C.). Ionic liquids have a number of uses that include replacing organic solvents in chemical processes and reactions, extracting organic compounds from aqueous waste streams, and as electrolytes in devices such as capacitors and batteries. This is because, unlike conventional organic solvents, ionic liquids are non-volatile and non-flammable. These properties are advantageous to help reduce losses to evaporation, eliminate volatile organic emissions, and improve safety.

Other properties of ionic liquids have also proved advantageous. For example, many ionic liquids have a broad temperature range at which they remain liquid and also are stable over a broad pH range. This is beneficial for high temperature processes with a demanding pH. Further, some ionic liquid systems can be used as both a solvent and catalyst. For example, [bmim]-$Al_2Cl_7$ and [emim]-$Al_2Cl_7$ can be employed as a solvent and catalyst in Friedel-Crafts reactions wherein bmim is 1-butyl-3methylimidazolium and emim is 1-ethyl-3-methylimidazolium.

For the aforementioned reasons, it would be desirable to discover new ionic liquid compounds with advantageous properties. It would further be desirable if such compounds could be made by simple processes with low amounts of waste and impurities.

Advantageously, new ionic liquid compounds have been discovered. The compounds comprise a Lewis acid anion and are made via simple processes that are capable of producing ionic liquids having a high purity.

DETAILED DESCRIPTION OF THE INVENTIONS

As used herein "ionic liquid" means a salt (or hydrate or solvate of the salt) comprising a cation and an anion that is a liquid at ambient or near ambient temperatures (i.e. having a melting point, or melting range, below about 100° C.). An ionic liquid may comprise two or more different salts, e.g., mixtures of salts comprising two or more different cations, anions, or both. Ionic liquids can be hydrated or solvated. Thus, both hydrates and solvates are considered to be within the definition of "ionic liquid."

As used herein "composition" includes a mixture of the materials that comprise the composition, as well as, products formed by the reaction or the decomposition of the materials that comprise the composition.

As used herein "derived from" means made or mixed from the specified materials, but not necessarily composed of a simple mixture of those materials. Substances "derived from" specified materials may be simple mixtures of the original materials, and may also include the reaction products of those materials, or may even be wholly composed of reaction or decomposition products of the original materials.

As used herein "halo" means chloro, bromo, fluoro, or iodo, alkyl means a monovalent alkane group which may be substituted with one or more heteroatoms such as nitrogen or oxygen, double bonds, or other substitutents. The type of the substituent is not particularly critical so long as the compound or mixture of compounds has the desired ionic liquid properties. Thus, the substituents usually may include typical and non-typical organic subsitituents such as those selected from the group consisting of alkyl, alkoxy, alkylthio, $SO_3H$, $NO_2$, halo, cyano, silyl, OH, and other suitable substituents. The substituent group itself may often be further substituted.

As used herein, "Lewis acid" is a substance that accepts or is capable of accepting an electron pair such as $AlCl_3$ and the like.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 and the like, are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

The ionic liquids of the present invention may comprise one or more compounds. Thus, the ionic liquid may be a pure compound or may be a mixture of compounds. Each compound comprises an anion or a mixture of anions and a cation or a mixture of cations as described below.

Anions

The anions of the present inventions typically have the formula $Al_yR_{3y+1}$ wherein y is greater than 0 and R is independently selected from an alkyl group or a halogen group. Y may be an integer but it also includes decimals when there are non-stoichiometric amounts of the aluminum anion. In these cases, the aluminum anion will be mixed with other anions such as halides. Thus, ionic liquids of the present inventions include compositions comprising, for example, a quaternary ammonium chloride mixed with a quaternary ammonium aluminum chloride. The aluminum chloride can be, for example, tetrachloroaluminate or heptachlorodialuminate.

The R group and the value of y in the anion are usually selected based on the desired properties of the ionic liquid. For example, if the ionic liquid is going to be used as a Friedel-Crafts catalyst then particularly preferred anions are aluminum chloride anions such as $AlCl_4$ and $Al_2Cl_7$.

When one or more R groups are a halogen group the halogen is preferably chloride, bromide or iodide. When one or more R groups is an alkyl group then the alkyl group should have a sufficient number of carbon atoms so that the ionic liquid has the desired properties. For example, if the ionic liquid is to be used as a catalyst then the total number of carbon atoms in the ionic liquid should be selected so as to maximize the catalyst's effectiveness and efficiency. The total number of carbon atoms may also affect other properties of the ionic liquid such as vapor pressure, dipole moment, polarity, etc.

In one embodiment, a carbon containing bridge between neighboring aluminum atoms is used to stabilize a dialuminum anion contained in the ionic liquid. The carbon containing bridge may contain alkyl, alcoxide and/or arene groups and substantially inhibit leaching of aluminum trichloride into the surrounding composition. For example, the ionic liquid may be used as a reaction solvent and/or catalyst and it would typically be undesirable for aluminum trichloride to leach into the process stream. The organic bridge is preferably selected to sufficiently stablize the dialuminate anion while maintaining sufficient activity for any desired catalytic functionality. The organic bridge is used to bond neighboring aluminum atoms that would otherwise be susceptible to leaching of aluminum trichloride. It is believed that the following anion structures would be useful to form ionic liquids while tending to prevent undesirable leaching of aluminum trichloride:

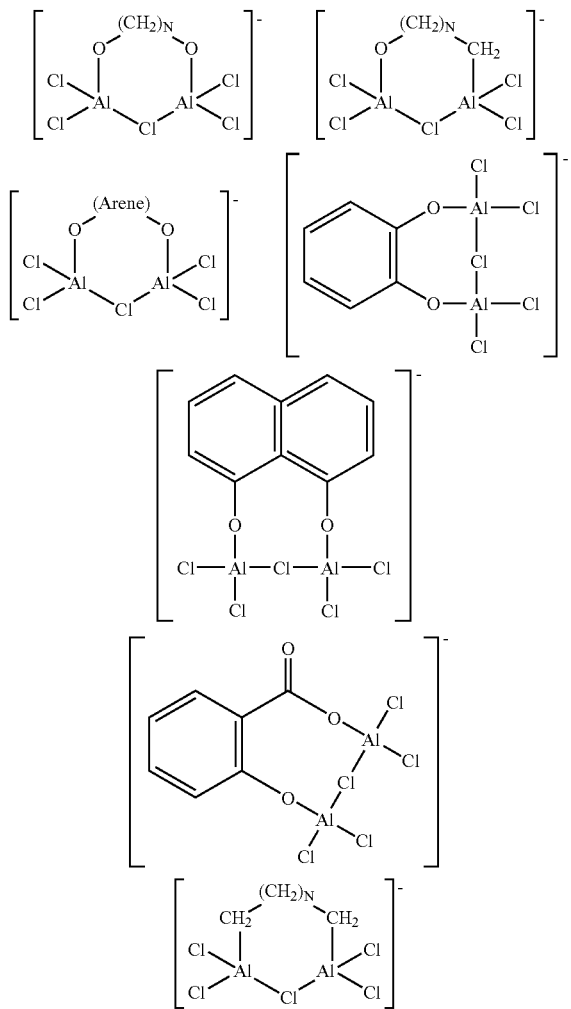

Cations

The cations of the compositions of the present inventions are generally selected from ammonium, sulfonium, and phosphonium cations wherein said cation has less than 14 total carbon atoms. By limiting the number of carbon atoms in the cation to less than 14 carbon atoms, an ionic liquid can be obtained which has a higher percentage of $Al_yR_{3y+1}$ per unit volume. This often facilitates reactivity and typically makes the ionic liquid a much better catalyst. In addition, it is often preferred that the ammonium, sulfonium, and phosphonium cations be saturated to be most effective, convenient, or cost-effective as catalysts.

A preferred cation is tetraalkylammonium. Depending on the desired ionic liquid properties it may be advantageous for one or more of the alkyl groups to be optionally substituted with one or more suitable substitutents. Suitable substituents include, for example, halogens such as chloride, bromide, or iodide. Particularly preferred tetralakylammonium cations include trimethylethyl ammonium, trimethyl chloromethyl ammonium, trimethylbutyl ammonium, and tributyl methyl ammonium. It is preferred that when the cation is triethylmethyl ammonium then the anion should be selected from aluminum bromide, or aluminum iodide.

Another preferred cation is N-alkyl substituted saturated heterocycles such as piperidinium and morpholinium. Pyrolidine-based cations can also be employed. In particular, piperidinium and pyrolidine-based cations substituted on the nitrogen with an alkyl group (or alkyl groups containing one or more ether groups or halide groups) such as—$(CH_2)_2OMe$, butyl, or propyl are particularly beneficial. The cation may include ether functionality (e.g., $NCH_2CH_2OCH_3^+$). The cation may include halogenated alkyl groups.

It has been found that several factors can be used to predict the ability of a given cation to form a salt that is liquid at or near ambient temperature. Cations having between 5 and 11 total carbon atoms, in the absence of heterocyclic structures, have been found to be useful in making molten salts with desirable melting point and phase behavior properties. Further, cations that are non-tetrahedrally symmetric tend to more readily form near ambient temperature molten salts. Additionally, the anion and the cation are preferably present in a molar ratio of about 2:1, respectively, ± about 10% (i.e., about 1.8 to 2.2 moles of anion for every mole of cation).

Processes to Make Compositions of the Present Inventions

The ionic liquids of the present inventions may be conveniently made by a number of different processes. One process which is suitable for making ionic liquids or mixtures of the present inventions comprises reacting a halide of the desired cation with a Lewis acid in the presence of an optional solvent. That is, the process for preparing a Lewis acid ionic liquid composition of the present inventions often comprises mixing an ammonium, sulfonium, or phosphonium halide with $Al_yR_{3y+1}$. The ammonium, sulfonium, or phosphonium halide preferably comprises less than 14 total carbon atoms.

The manner of contacting the two or more compounds to form the ionic liquid is not particularly important so long as the desired reaction occurs. Generally, the compounds can be mixed in any order, can be formed in situ, or can be mixed together with a solvent which is at least partially miscible and does not significantly react with any of the compounds. Preferred solvents include substances that give good reflux conditions like cyclohexane, alkanes, toluene, or mixtures thereof.

The starting compounds are often readily available and, in addition, many syntheses are available to those skilled in the art to make the desired starting compounds. The mixing conditions may vary depending on the specific compounds employed and the desired product. In most instances, it is acceptable to contact the compounds and the optional solvent at ambient pressure and a temperature high enough for the reaction to occur efficiently but not so high as to decompose or boil off any starting compound.

The manner in which the desired temperature is achieved and maintained is not particularly critical. Often any heating element may be employed as the compounds are mixed or the starting compounds can be heated separately and then mixed. Similarly, any vessel or reactor can be employed so long as it is of adequate size and material. Often it is beneficial to employ a stirring means to facilitate the reaction.

Generally, the temperature is maintained for at least a sufficient time until the desired reaction has occurred to the desired extent. In some instances, it may be desirable to maintain the temperature for a longer time than it takes to complete the reaction. In this manner, any lower boiling components that are formed as byproducts or present as solvents can be removed by boiling if the temperature is high enough to do so.

The amount of each of the starting compounds may vary depending upon the desired yield. In general, since the reaction is very exothermic the ratio of ammonium, sulfonium, or phosphonium halide to $Al_yR_{3y+1}$ should be selected so that any heat produced by the reaction is controlled. While for some starting compounds this may be a stoichiometric ratio, generally, one of the starting compounds should be in molar excess to most effectively control the heat of the reaction. However, as one skilled in the art will appreciate, different reaction conditions may alter the ratio of reactants at which the optimum yield and optimum control of reaction heat occurs. In addition, if an ionic liquid is desired with a higher percentage of $Al_yR_{3y+1}$ then a molar amounts of the aluminum starting material should be increased.

If one desires to make an ionic liquid mixture comprising two or more different salts, then it is readily accomplished by employing a mixture of three or more different compounds so that a variety of salts are formed. The resulting ionic liquid salt mixture can then be used as a mixture or, if desired, individual salts can be separated by routine means.

If necessary, the ionic liquid or ionic liquid mixture may be recovered from the solvent and/or reaction mixture by any suitable means the most efficient of which may vary depending upon the type and desired purity of the ionic liquid or mixture. Preferable means of recovery include rotary evaporation or distillation, azeotropic distillation, ion chromatography, liquid liquid extraction, crystallization, pervaporization, drying agents, and reverse osmosis.

In one embodiment, azeotropic distillation can be employed to remove water from the source of cation prior to the addition of a chloroaluminate to form the ionic liquid. For example, amine, phosphine, or mercaptan can be reacted with an alkyl halide in an organic solvent to form a cation as a halide salt. The organic solvent is preferably a hydrocarbon. Exemplary organic solvents include cyclohexane, toluene, octane, and hexane. Heat can then be added to the mixture to cause the organic solvent to boil, thereby forming an azeotrope between the organic solvent and any water present. Most or all of the water is preferably removed by azeotropic distillation. The halide salt (source of cation) can then be reacted with the chloroaluminate (source of anion) to form an ionic liquid. The solvent is preferably refluxed to remove at least a portion of heat generated by reaction via the boiling and condensation of the solvent.

The organic solvent can be removed from the ionic liquid by use of a liquid extraction. The organic solvent preferably forms a barrier layer on top of the ionic liquid prior to separation to inhibit moisture from the air from contacting the ionic liquid. After the liquid extraction, the residual organic solvent may be separated from the ionic liquid via distillation under vacuum conditions. The organic solvent, which may contain impurities from the reactants (such as aluminum chloride), is preferably washed with water prior to being recycled back into the reaction mixture for reuse.

Characteristics and Uses of Ionic Liquids of the Present Inventions

The purity of ionic liquids produced by the processes of this inventions can often be greater than 50%, preferably greater than 60%, more preferably greater than 70%, most preferably greater than 80%. This is often advantageous for processes that require high purity materials such as in the electronics industry. The ionic liquids are useful in many processes as a substitute for an organic solvent or catalyst or in mixtures with one or more added solvents or catalysts. Some ionic liquids of the present inventions are particularly useful catalysts for dimerization or trimerization of olefins, for Friedel-Crafts reactions, or for hydrocarbon cracking. Further, the ionic liquids of the present invention are often highly reactive and even react with water.

The following examples are not intended to limit the inventions, but rather, are intended only to illustrate a few specific ways the instant inventions may be employed.

EXAMPLE 1

Synthesis of Trimethylethyl Ammonium Aluminum Chloride

Trimethylethylammonium chloride (940 g) was added to 1 liter cyclohexane in a 3 neck flask fitted with a thermocouple, a solid addition funnel, and a Dean-Stark trap with a reflux condenser. The mixture was heated until the solvent boiled and the reflux is continued until no more water collected in the trap. At this point, the trap and the heating mantle were removed and $AlCl_3$ was added (2009 g) gradually over several hours. The mixture gradually reacted to form a lower liquid layer with unreacted solid tetraalkylammonium chloride, which disappeared as the $AlCl_3$ was added. By the time the $AlCl_3$ addition was complete, all the solids had dissolved, and the mixture comprised two liquid phases. The mixture was allowed to cool, and the contents of the flask were transferred to a separatory funnel. The lower layer was collected under nitrogen, and the cyclohexane that was still dissolved in the ionic liquid was stripped off under vacuum. The yield of the final product (trimethylethylammonium heptachlorodialuminate) was nearly quantitative.

EXAMPLES 2–5

The ionic liquids of Examples 2–5 in Table 1 below were made substantially as in the same manner as Example 1 except that the starting compounds of Table 1 are employed.

TABLE 1

| Example | Starting compound | Ionic Liquid |
| --- | --- | --- |
| 2 | N-alkyl substituted piperidinium chloride | N-alkyl substituted piperidinium heptachlorodialuminate |
| 3 | trimethyl chloromethyl ammonium chloride | trimethyl chloromethyl ammonium heptachlorodialuminate |

TABLE 1-continued

| Example | Starting compound | Ionic Liquid |
|---|---|---|
| 4 | trimethylbutyl ammonium chloride | trimethylbutyl ammonium heptachlorodialuminate |
| 5 | tributyl methyl ammonium chloride | tributyl methyl ammonium heptachlorodialuminate |

Of course in any of the aforementioned examples the molar ratio of starting compounds can be adjusted to vary the ratio of specific cations and specific anions in the product. In addition, the molar ratios and starting materials can be varied so that the anion of the ionic liquid is, for example, tetrachloroaluminate, tetrabromoaluminate or the like.

EXAMPLES 6–12

The ionic liquids of Examples 6–12 in Table 2 below were made substantially as in the same manner as Example 1 except that the ammonium salts of Table 2 were employed with $AlCl_3$ in the amounts detailed below. In some cases, vacuum drying was used instead of azeotropic distillation to dry the chloride salt.

TABLE 2

| Example | Ammonium Salt | Moles of Ammonium Salt | Moles of $AlCl_3$ | Product |
|---|---|---|---|---|
| 6 | MeBu3N Cl | 0.090 | 0.193 | liquid |
| 7 | Me3PentylN Cl | 0.006 | 0.013 | liquid |
| 8 | Me3ButylN Cl | 0.008 | 0.016 | liquid |
| 9 | MeEt3N Cl | 0.006 | 0.012 | liquid |
| 10 | Me2Et2N Cl | 0.078 | 0.157 | liquid |
| 11 | Cl-CH2-NMe3 Cl | 0.025 | 0.049 | liquid |
| 12 | N-methyl-N-Butyl Pyrolidinium Cl | 0.042 | 0.084 | liquid |

What is claimed is:

1. A Lewis ionic liquid composition comprising:
   (a) a cation selected from ammonium, sulfonium, and phosphonium cations wherein said cation has less than 14 total carbon atoms; and
   (b) an anion having the formula $Al_yR_{3y+1}$ wherein y is greater than 0 and R is independently selected from the group consisting of an alkyl group and a halogen group with the proviso that when the cation is triethylmethyl ammonium the anion is selected from aluminum bromide, or aluminum iodide;
and further comprising a salt comprising quaternary ammonium cations and halide anions.

2. The composition of claim 1 wherein the cation is tetralkylammonium.

3. The composition of claim 1 wherein the anion is an aluminum chloride anion.

4. A Lewis acid ionic liquid composition comprising:
   (a) a cation selected from ammonium, sulfonium, and phosphonium cations wherein said cation has less than 14 total carbon atoms; and
   (b) an anion having the formula $Al_yR_{3y+1}$ wherein y is greater than 0 and R is independently selected from the group consisting of an alkyl group and halogen group with the proviso that when the cation is triethylmethyl ammonium the anion is selected from aluminum bromide, or aluminum iodide;
wherein the cation is tetralklammonium and wherein one or more of the alkyl groups is substituted with an ether group.

5. A Lewis acid ionic liquid composition comprising:
   (a) a cation selected from ammonium, sulfonium, and phosphonium cations wherein said cation has less than 14 total carbon atoms; and
   (b) an anion having the formula $Al_yR_{3y+1}$ wherein y is greater than 0 and R is independently selected from the group consisting of an alkyl group and halogen group with the proviso that when the cation is triethylmethyl ammonium the anion is selected from aluminum bromide, or aluminum iodide;
wherein the cation is tetralkylammonium and wherein one or more of the alkyl groups is substituted with one more halogens.

6. A Lewis acid ionic liquid composition comprising:
   (a) a cation selected from ammonium, sulfonium, and phosphonium cations wherein said cation has less than 14 total carbon atoms; and
   (b) an anion having the formula $Al_yR_{3y+1}$ wherein y is greater than 0 and R is independently selected from the group consisting of an alkyl group and halogen group with the proviso that when the cation is triethylmethyl ammonium the anion is selected from aluminum bromide, or aluminum iodide;
wherein the cation is selected from trimethylethyl ammonium, bis(N-alkyl) substituted piperidinium, trimethyl chloromethyl ammonium, trimethylbutyl ammonium, and tributyl methyl ammonium.

7. The composition of claim 6 wherein the piperidinium is substituted with a methyl and one group selected from the group consisting of —$(CH_2)_2$OMe, butyl, and propyl.

8. The composition of claim 6 wherein the anion is an aluminum chloride anion.

9. The composition of claim 7 wherein the anion is an aluminum chloride anion.

10. A process for preparing an ionic liquid composition comprising reacting a cation source with an anion source to from an ionic liquid that compromises:
    (a) a cation selected from ammonium, sulfonium, and phosphonium cations wherein said cation has less than 14 total carbon atoms; and
    (b) an anion having the formula $Al_yR_{3y+1}$ wherein y is greater than 0 and R is independently selected from the group consisting of an alkyl group and halogen group with the proviso that when the cation is triethylmethyl ammonium the anion is selected from aluminum bromide, or aluminum iodide;
wherein the $Al_yR_{3y+1}$ is in molar excess of the ammonium, sulfonium, or phosphonium halide.

11. A process for preparing an ionic liquid composition comprising reacting a cation source with an anion source to from an ionic liquid that compromises:
    (a) a cation selected from ammonium, sulfonium, and phosphonium cations wherein said cation has less than 14 total carbon atoms; and
    (b) an anion having the formula $Al_yR_{3y+1}$ wherein y is greater than 0 and R is independently selected from the group consisting of an alkyl group and halogen group with the proviso that when the cation is triethylmethyl ammonium the anion is selected from aluminum bromide, or aluminum iodide;
and further comprising contacting the cation source with a solvent and removing heat generated during reaction of the cation source and anion source by evaporation and condensation of the solvent.

12. The process of claim 10 wherein the ratio of ammonium, sulfonium, or phosphonium halide with $Al_yR_{3y+1}$ is such that any heat produced by the reaction is controlled.

13. The process of claim 11 wherein the ammonium, sulfonium, or phosphonium halide is in molar excess of the $Al_yR_{3y+1}$.

14. The process of claim 11 wherein the solvent is selected from the group consisting of cyclohexane, an alkane, and toluene.

15. An ionic liquid composition, comprising:
    (a) a cation comprising a pyrolidine-based structure; and
    (b) an anion having the formula $Al_yR_{3y+1}$ wherein y is greater than 0 and R is independently selected from the group consisting of an alkyl group and halogen group.

16. An ionic liquid composition, comprising:
    (a) a cation selected from the group consisting of ammonium, sulfonium, and phosphonium cations, said cation being non-tetrahedrally symmetric;
    (b) a anion containing at least two aluminum atoms, the aluminum atoms being bonded together by an organic bridge to stabilize the chloroaluminate anion and inhibit leaching from the chloroaluminate anion.

17. The composition of claim 16, wherein the organic bridge comprises an alcoxide group to inhibit leaching of aluminum trichloride during use.

18. The composition of claim 16, wherein the organic bridge comprises an arene group to inhibit leaching of aluminum trichloride during use.

19. The composition of claim 16, wherein the cation is sourced from an ammonium salt selected from the group consisting of MeBu3N Cl, Me3PentylN Cl, Me3ButylN Cl, MeEt3N Cl, Me2Et2N Cl, Cl—CH2—NMe3 Cl, and N-methyl-N-Butyl Pyrolidinium Cl.

20. An ionic liquid selected from the group consisting of N-alkyl substituted piperidinium heptachlorodialuminate, trimethyl chloromethyl ammonium heptachlorodialuminate, trimethylbutyl ammonium heptachlorodialuminate, and tributyl methyl ammonium heptachlorodialuminate.

21. A process for synthesizing an ionic liquid, comprising:
    (a) reacting a first reactant with an alkyl halide in an organic solvent, thereby forming a cation as a halide salt, the first reactant being selected from the group consisting of amine, phosphine, and mercaptan;
    (b) adding heat to organic solvent to cause it to boil, thereby forming an azeotrope between the organic solvent and water;
    (c) removing water from the mixture by azeotropic distillation; and
    (d) contacting the halide salt with a chloroaluminate to form an ionic liquid.

22. The process of claim 21, further comprising refluxing the solvent to remove at least a portion of heat generated by reaction.

23. The process of claim 21, further comprising separating the solvent from the ionic liquid by liquid extraction.

24. The process of claim 21, further comprising separating the organic solvent from the formed ionic liquid by distillation under vacuum conditions.

25. The process of claim 21, further comprising removing a portion of the organic solvent from the mixture by distillation, removing impurities from the portion of the organic solvent, and recycling the portion of the organic solvent back into the mixture.

26. The process of claim 21, wherein the organic solvent is cyclohexane.

27. The composition of claim 16, wherein the anion has a structure that is selected from the group consisting of the following:

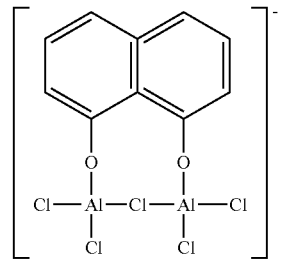

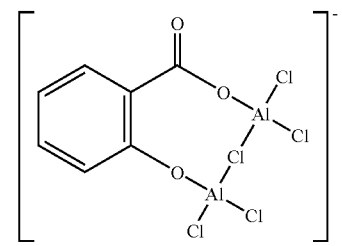

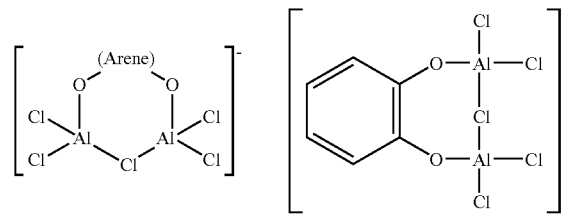

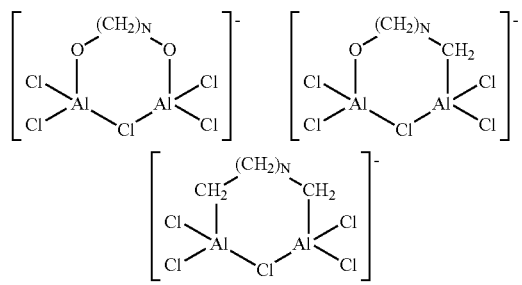

* * * * *